(12) United States Patent
Roncaglioni et al.

(10) Patent No.: US 7,327,825 B2
(45) Date of Patent: Feb. 5, 2008

(54) EQUIPMENT FOR MAMMOGRAPHY

(75) Inventors: Aurélie Roncaglioni, Bois d'Arey (FR); Pascal Salazar-Ferrer, Chevreuse (FR)

(73) Assignee: General Electric Company, Schenectady, NY (US)

( * ) Notice: Subject to any disclaimer, the term of this patent is extended or adjusted under 35 U.S.C. 154(b) by 187 days.

(21) Appl. No.: 11/255,723

(22) Filed: Oct. 21, 2005

(65) Prior Publication Data
US 2006/0115041 A1 Jun. 1, 2006

(30) Foreign Application Priority Data
Nov. 26, 2004 (FR) .................................. 04 12573

(51) Int. Cl.
*A61B 6/04* (2006.01)
(52) U.S. Cl. ......................................... 378/37; 378/177
(58) Field of Classification Search .................. 378/37, 378/177
See application file for complete search history.

(56) References Cited

U.S. PATENT DOCUMENTS

| 3,556,081 | A | * | 1/1971 | Jones | 600/437 |
|---|---|---|---|---|---|
| 4,097,748 | A | * | 6/1978 | Monvoisin | 378/146 |
| 4,979,196 | A | * | 12/1990 | Lieutaud et al. | 378/37 |
| 5,083,305 | A | | 1/1992 | Tirelli et al. | |
| 5,189,686 | A | * | 2/1993 | Hixson, Sr. | 378/37 |
| 5,594,769 | A | * | 1/1997 | Pellegrino et al. | 378/37 |
| 5,820,552 | A | * | 10/1998 | Crosby et al. | 600/407 |
| 6,296,386 | B1 | * | 10/2001 | Heidsieck et al. | 378/189 |
| 6,765,985 | B2 | * | 7/2004 | Marie et al. | 378/37 |
| 6,883,194 | B2 | * | 4/2005 | Corbeil et al. | 5/601 |
| 6,987,831 | B2 | * | 1/2006 | Ning | 378/37 |
| 7,133,490 | B2 | * | 11/2006 | Muller et al. | 378/37 |
| 2006/0262898 | A1 | * | 11/2006 | Partain et al. | 378/37 |

* cited by examiner

*Primary Examiner*—Edward J. Glick
*Assistant Examiner*—Thomas R. Artman
(74) *Attorney, Agent, or Firm*—Cantor Colburn LLP

(57) ABSTRACT

Equipment for an apparatus for mammography having a C-shaped arm having a radiation source at one of its ends and, at its other end, a breast support plate and image acquisition. The equipment is at the level of a portion on the side of the breast support plate or in the prolongation of such a portion, close to the main body of the C-shaped arm. The equipment has a shape with at least one projection and/or hollow set in the external surface of the apparatus and defines a zone able to be used as a secondary handle and/or armrest.

20 Claims, 5 Drawing Sheets

EQUIPMENT FOR MAMMOGRAPHY

This application claims the benefit of a priority under 35 USC 119(a)-(d) to French Patent Application No. 0412573 filed Nov. 26, 2004, the entire contents of which are hereby incorporated by reference.

The present invention relates to radiology and in particular to an apparatus for mammography.

Conventionally, as shown in FIG. 1, an apparatus for mammography comprises a C-shaped arm 1, which has a means 2 for providing radiation at one of its ends, for example an X-ray tube and which, at its other end, has means 4 for image acquisition, such as a cassette tray or digital detector, as well as means 3 for support, such as a breast support plate, which can be removable if necessary. Means 5 for compression, such as a plate or pad, is adjustable in height relative to plate 3, is provided facing plate 3. The C-shaped arm is mounted on a frame 20 relative to which it can be pivoted, particularly around a horizontal axis.

Mammography images are generally taken with the patient standing upright facing towards the apparatus. The operator positions the breast on the plate 3, in such a way as to spread it as evenly as possible, and then compresses it by means of plate 5. In this way, one tries to enter the largest possible portion of the breast within the X-ray beam and thus to obtain the greatest possible coverage of the breast being examined, as far as and including the pectoral muscle. In order to help obtain this result, it is desirable to have the patient's arm in a position on the side of the part of the chest being observed, with the forearm lifted slightly.

Furthermore, it is important for the patient to remain completely still in this position during the totality of the exposure time, which can be more than a few seconds. Therefore, she must feel relatively relaxed in this position, comfort and stability being essential for optimized image quality.

This is why a lateral handle is generally provided on an apparatus for mammography, that can also serve for maneuvering rotation of the arm 1, if this rotation is manual, or can just be for the use of the patient, who stretches along the C-shaped arm (element 6, tubular for example, projecting along it), and which the patient can grasp in order to hold up the arm.

A lateral handle is generally satisfactory for most examination cases. Nonetheless, this handle can be a source of significant limitations having a direct impact on image quality and expected comfort, especially during certain specific examination procedures used in some countries. In particular, especially when the C-shaped arm is tilted, the patient holding the handle may tend to contract the muscles of the arm or shoulder, thus reducing the visibility of the pectoral muscle.

BRIEF DESCRIPTION OF THE INVENTION

An embodiment of the present invention relates to an apparatus for mammography comprising means for providing radiation, means for support of a breast and means for image acquisition. At the level of a portion on the side of the means for support of a breast or in a prolongation of such a portion, which may be close to the main body of a C-shaped arm, an equipment is provided that has a shape with at least one projection and/or hollow set in the external surface of the equipment and defining a zone able to be used as a secondary handle and/or armrest.

BRIEF DESCRIPTION OF THE DRAWINGS

An embodiment of the invention will become even clearer from the following description, given as a purely illustrative and non-limiting example, and with reference to the attached figures, in which.

DETAILED DESCRIPTION OF THE INVENTION

Figure 1:
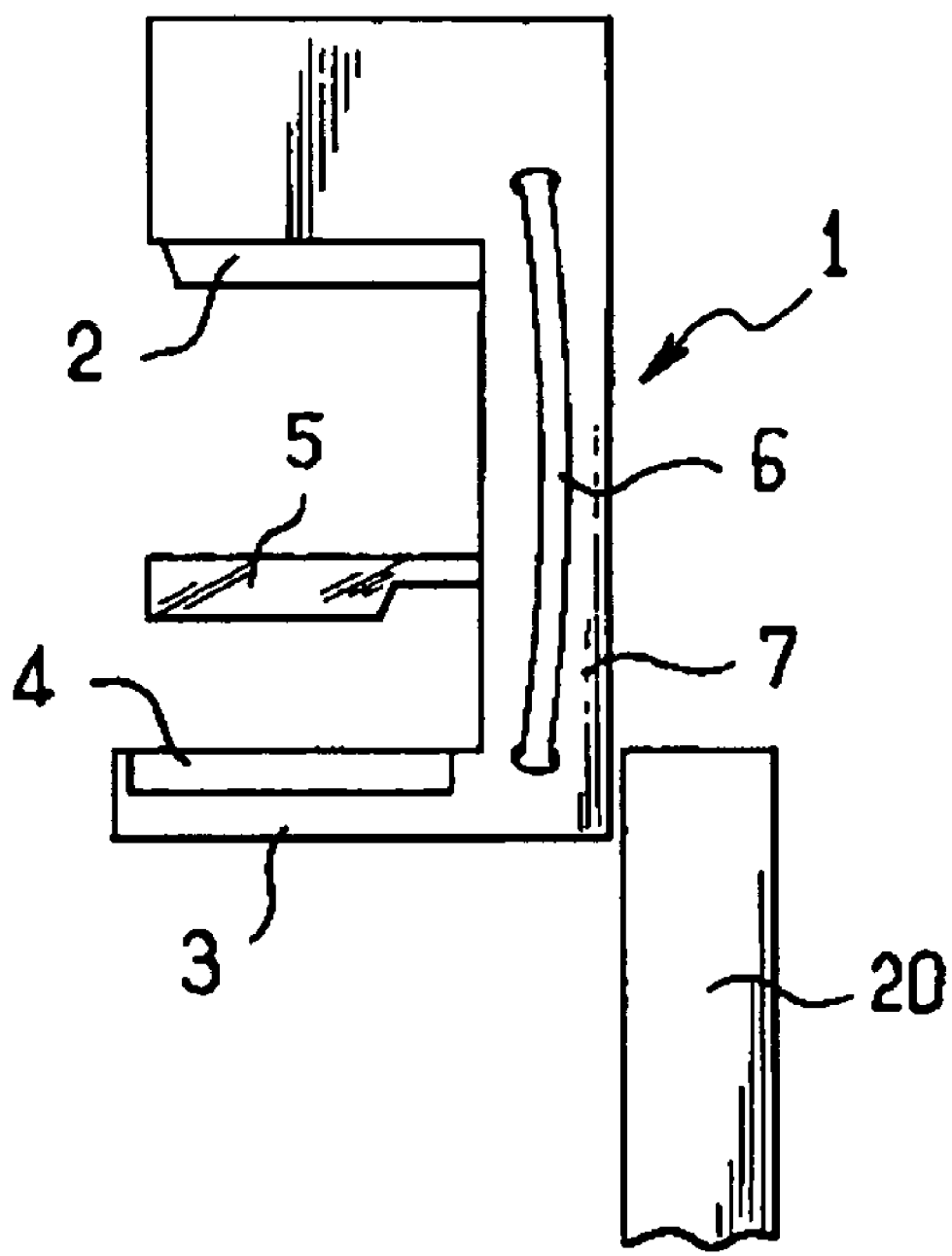
FIG. 1 is a diagrammatic illustration of a conventional apparatus for mammography.
Figure 2:
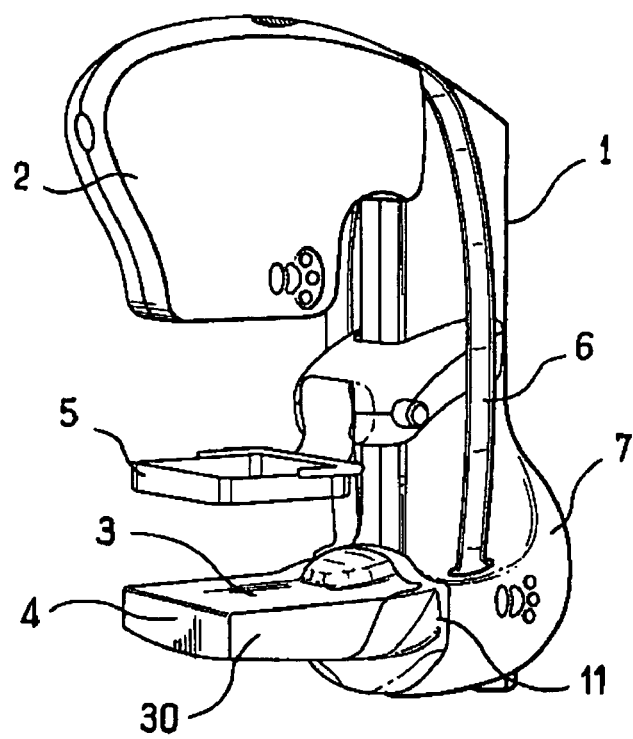
FIG. 2 is a general illustration of equipment for a mammography apparatus according to an embodiment of the invention.

A radiological apparatus for mammography, as shown in FIG. 2, comprises a C-shaped arm 1, means 2 for providing a source of radiation, such as X-rays, means 3 support of a breast, such as a plate, means 4 for image acquisition means and means 5 for compression, such as adjustable plate 5. The means 4 for image acquisition may comprise, for example, a cassette tray of the Potter Bucky type or a digital detector, and is held by the end of the C-shaped arm or by the breast support plate 3. The C-shaped arm 1 has a main body 7, from each side of which extend two principal tubular handles 6.

Figure 3:
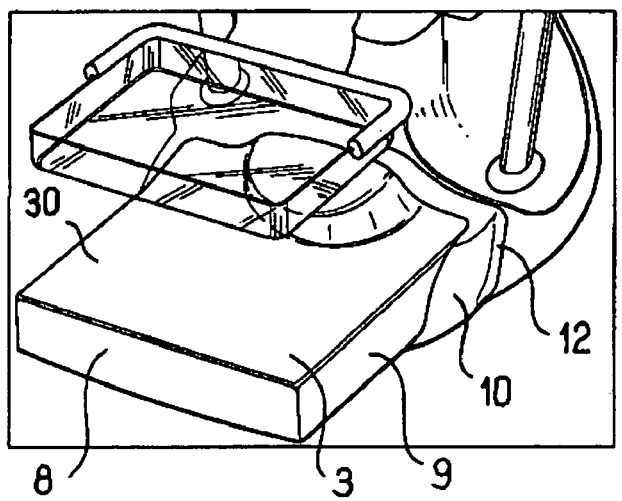
FIG. 3 is a front view in perspective of a detail of this equipment, and, in particular, a handle for the equipment.
Figure 4:
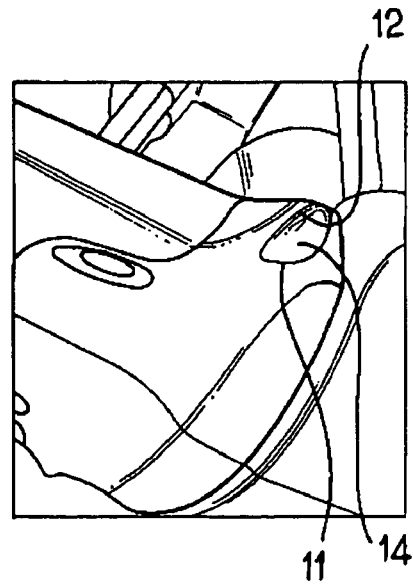
FIG. 4 is a drawing according to another perspective direction of the handle shown in FIG. 2.

The breast support plate 3 comprises an upper surface of a cover 30, made for example out of plastic material, carbon composite etc., with the general shape of a flat parallelepiped, having an end edge 8 facing the patient, as shown in FIG. 3, and having lateral edges 9. The C-shaped arm may have a shell or cover assembly, for example in plastic or composite material, etc. The general shape of this cover assembly joins the lateral edges 9 of the cover 30, with continuous transition zones 10. At the level of these lateral transition zones 10, that is to say on each side of the support plate 3, near the body 7, the cover assembly of the C-shaped arm has a hollow and/or projecting shape 11, able to be used as will be described later, as a handle or an armrest.

In the embodiment illustrated, a projecting zone 12 can be provided, particularly to function as a handle. In an exemplary embodiment, the projecting zone 12 is located at a distance of the order of 250 to 500 millimeters from the end edge 8 of the support plate 3.

Hollow(s) and/or projection(s) 11 can be set in the external surface of the apparatus. The hollow(s) and/or projection(s) 11 can be made from material in the cover assembly of the C-shaped arm. The hollow(s) and/or projection(s) 11 could also be molded with the cover 30, defining the breast support plate 3, if the transition zones 10 were made from material with them. If the C-shaped arm does not have any cover assembly and is molded in a single piece, the hollow(s) and/or projection(s) of the shape 11 on the external surface of the piece can be molded directly with it.

Figure 5A:
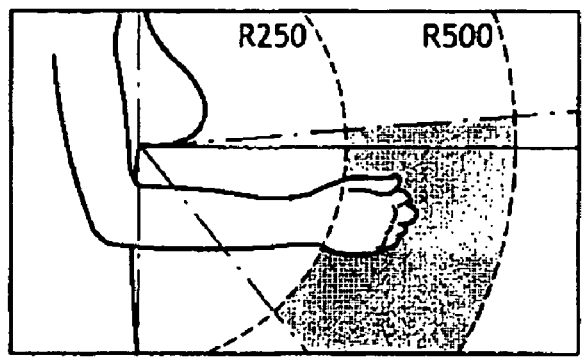
FIGS. 5a to 5f illustrate the definition of different possible parameters for positioning and orienting the handle of FIGS. 2 and 3.
Figure 5B:
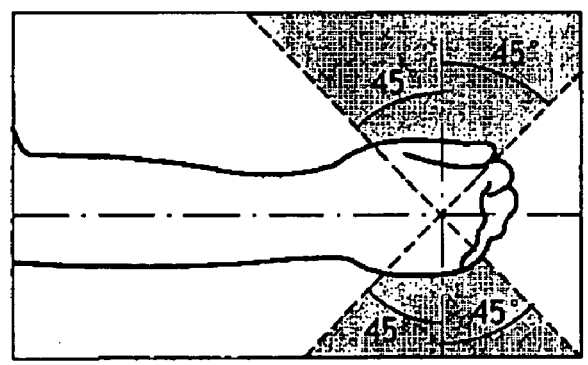
Figure 5C:
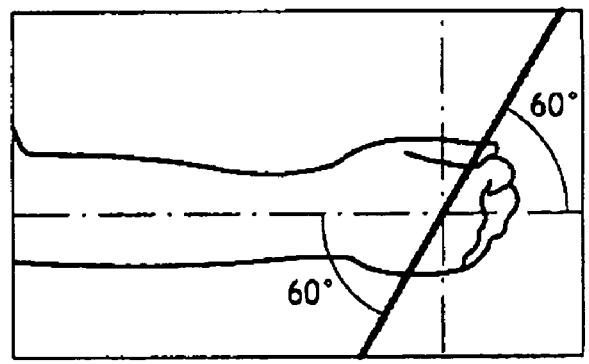
Figure 5D:
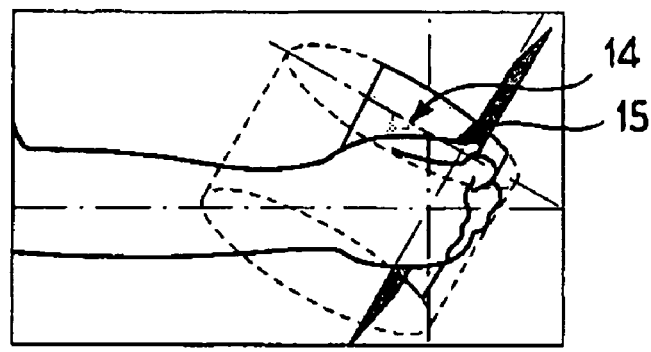
Figure 5E:
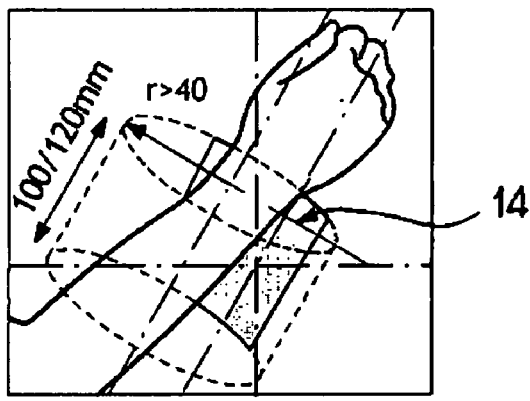
Figure 5F:
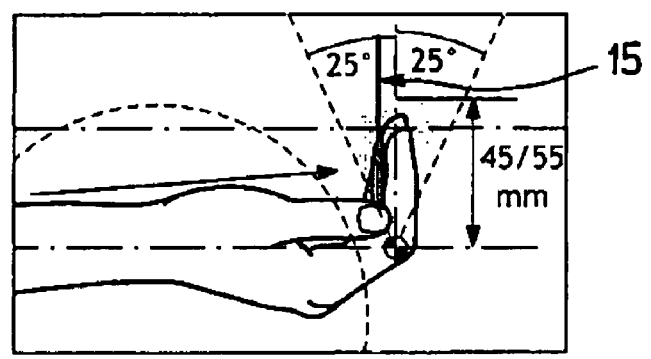

FIGS. 5a to 5f illustrate, as an example, the choice of different parameters able to define the shape 11 and in particular the projecting zone 12. Thus, the projecting zone 12 is for example oriented with an angle comprising between +10 degrees and −50 degrees relative to the general plane of the plate 3 (FIG. 5a). The front face of the projecting shape 12, that is the face of the side of the end edge 8, combines with a general shape made from a portion of a cylinder 14, to define a form that can be used as an armrest by the patient. The axis of the base cylinder corresponding to this cylindrical shape is oriented to make an angle of between ±45 degrees (FIG. 5b) relative to the perpendicular to the mean direction of the patient's arm, meaning relative to the perpendicular to the general plane of plate 3. For example, this angle is of the order of 60 degrees (see FIG. 5c). The projecting shape prolongs the general cylinder arc shape by extending in a general plane 15 (FIG. 5d) whose orientation is provided in particular by the angle of the zone 12 relative to plate 3 (angle of FIG. 5a). Thus, in this example, the general cylinder arc shape and the projecting shape prolonging it make it possible to fulfill both handle and armrest functions. The projecting shape 12 extending along the general plane 15 fulfills the function of secondary handle that can be used by the patient to remain still in certain positions. The general cylindrical shape 14 can itself act, as shown in FIG. 5e, as an armrest. The cylindrical portion 14 forming the armrest can, for example, be of the order of 50 to 250 millimeters long (100 to 120 millimeters for example) with a radius greater than 40 millimeters. FIG. 5f shows other possible parameters for the general plane 15 of the projecting part. This general plane can be oriented at an angle of ±25 degrees around the perpendicular to the mean direction of the patient's arm, meaning relative to the general plane of plate 3. For example, it makes a 90 degrees angle relative to the general direction of the patient's arm. The height of the projecting shape can be 45 to 55 millimeters.

Figures 6A, 6B, 6C, 6D:
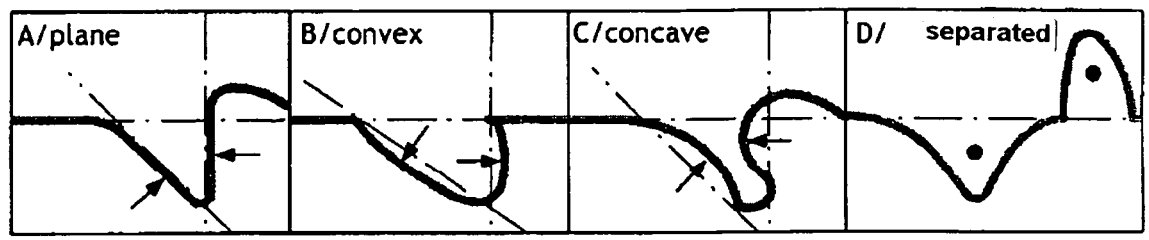
FIGS. 6a to 6d illustrate four possible cross-sections for the handle.

Different cross-section shapes are also possible. Thus, as shown in FIG. 6a, the projecting zone 12 can have a general triangular cross-section, the front and back surfaces (relative to edge 8) of the projecting part being closely plane. As a variant, zone 12 can be of a general convex shape (FIG. 6b) or of a general concave shape (FIG. 6c). Alternately, as shown in FIG. 6d, the armrest and handle functions can be distinct projections and hollows. In FIG. 6d, the projecting part is formed to carry out the function of armrest. The handle function is produced by a hollow, also made from material in the shell, and located to the rear relative to the projecting part 12. The two zones making these two functions possible are marked in FIG. 6d by separate dots.

Figure 7A:
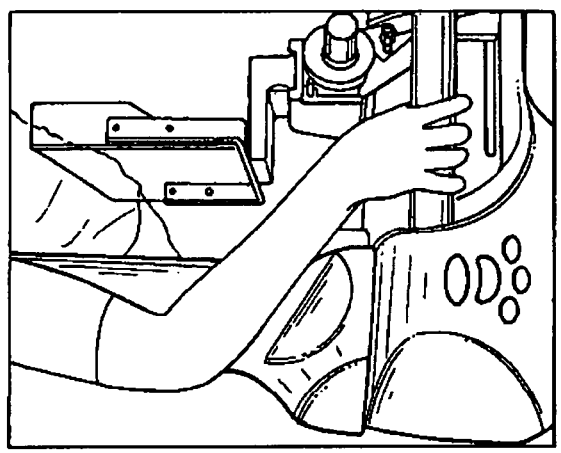
FIGS. 7a and 7b are drawings of a set of equipment from the preceding figures.
Figure 7B:
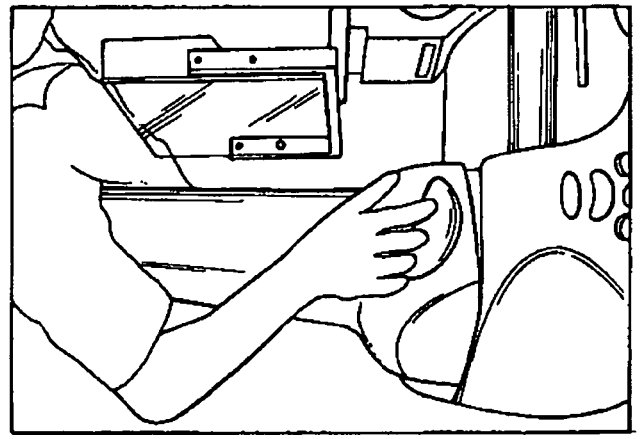

As shown by FIGS. 7a and 7b, the general appearance of the apparatus for mammography is generally unchanged and the use of projections and/or hollows made from material to carry out the handle and/or armrest function takes up only limited space.

In these figures it can also be understood that the handle and armrest functions allowed by the structure just described above make it possible to tilt the equipment while still offering very high comfort for the patient, which favors good image quality.

The shape 11 with hollow(s) and/or projection(s) can be made of the same substance as the apparatus shell, or yet again in another substance. Plastic, resin fiber composite, expanded polymer foam or metal frame materials are possible.

In order to improve the patient's comfort, one can provide: at the level of the forearm, a more flexible texture (softer to the touch) and/or at the level of the holding zone receiving the fingertips, a surface to limit sliding. Such characteristics can be obtained by modifying the surface during molding or by depositing material (deposit of a sheet of flexible or anti-slip material for example). For example, this shape forming a handle or armrest can be made from material with an external cover assembly for the C-shaped arm and/or for the breast support plate.

It is to be noted that such a structure with such a shape forming a handle and/or armrest, set in the external surface of the equipment, does not in any way reduce the accessibility of the equipment and does not limit its maneuverability, contrary to the case of a secondary handle being provided on the equipment, fixed projecting from it.

In addition, such a secondary handle would be difficult to fix on the equipment and would require very specific anchoring means, particularly in the case of mammography equipment with a cover assembly or shell in plastic or composite material etc.

In addition, while an embodiment of the invention has been described with reference to exemplary embodiments, it will be understood by those skilled in the art that various changes may be made in the function and/or way and/or result and equivalents may be substituted for elements thereof without departing from the scope and extent of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element or feature from another. Furthermore, the use of the terms a, an, etc. do not denote a limitation of quantity, but rather denote the presence of at least one of the referenced element or feature.

What is claimed is:

1. An apparatus for mammography comprising:
   a body;
   means for providing a radiation source, coupled to said body;
   means for supporting a breast coupled to said body, said means for supporting a breast including a top surface and a side surface;
   means for image acquisition coupled to said body; and
   a handle surface between said side surface and said body, said handle surface having a hollow portion in said handle surface and said hollow defining a zone able to be used as a secondary handle and/or armrest.

2. The apparatus according to claim 1 wherein the handle surface includes an external cover assembly integrally molded with said means for supporting a breast.

3. The apparatus according to claim 1 wherein said handle surface is at an angle to said side surface and said top surface to form an armrest.

4. The apparatus according to claim 3 wherein said handle surface is oriented at an angle comprising between approximately 10 degrees and 50 degrees relative to said top surface of the means for supporting a breast.

5. The apparatus according to claim 3 further comprising a means for supporting a breast further includes a front surface generally perpendicular to said top surface and said side surface wherein said handle surface is located in a zone at a distance comprising approximately between 250 to 500 millimeters from front surface of said means for supporting a breast.

6. The apparatus according to claim 3 wherein the said handle surface extends according to a general plane oriented at an angle approximately of ±25 degrees relative to said side surface of the means for support of a breast.

7. The apparatus according to claim 6 wherein the said handle surface extends according to a general plane closely perpendicular to the means for support of a breast.

8. The apparatus according to claim 6 wherein the handle surface has a height of approximately 45 to 55 millimeters.

9. The apparatus according to claim 1 wherein said handle surface includes a cylinder arc whose axis is oriented to form an angle of approximately ±45 degrees relative to the perpendicular to a general plane of the means for support of a breast.

10. The apparatus according to claim 9 wherein the cylinder arc portion has a length of approximately 50 to 250 millimeters.

11. The apparatus according to claim 9 wherein the cylinder arc portion has a length of approximately 100 to 120 millimeters.

12. The apparatus according to claim 9 wherein the cylinder arc portion has a radius greater than 40 millimeters.

13. The apparatus according to claim 1 wherein said handle surface forms an armrest, and said hollowed part forming a handle.

14. The apparatus according to claim 13 wherein the zone forming an armrest has a more flexible and/or softer texture than the rest of the apparatus.

15. The apparatus according to claim 14 wherein the zone forming a handle has an anti-slip zone.

16. The apparatus according to claim 1 wherein said handle surface hollow portion has a general triangular cross-section or a general convex shape or a general concave shape.

17. The apparatus according to claim 1 wherein said handle surface includes projections such that a projecting part is formed to carry out the function of armrest and a handle function is produced by said hollow portion.

18. The apparatus for mammography comprising:
means for providing a radiation source;
means for supporting a breast;
means for image acciuisition means;
an equipment at the level of a portion on the side of means for support of the breast or along the prolongation of such a portion, having a shape with at least one projection and/or hollow set in the external surface and defining a zone able to be used as a secondary handle and/or armrest;
wherein said equipment includes a cylinder arc whose axis is oriented to form an angle of approximately 60 degrees relative to the perpendicular to the general plane of the means for support of a breast.

19. An apparatus for mammography comprising:
a body;
a handle mounted to said body;
means for providing a radiation source mounted to said body;
means for image acquisition means mounted to said body;
a support plate mounted to said body, said support plate positioned between said means for providing radiation and said means for image acquisition, said support plate including a side surface; and,
a handle surface extending between said side surface and said body, said handle surface having a hollow portion in said handle surface.

20. The apparatus according to claim 19 wherein said handle surface oriented at an angle relative to said top surface and said side surface.

* * * * *